(12) United States Patent
Lee

(10) Patent No.: US 11,826,212 B2
(45) Date of Patent: Nov. 28, 2023

(54) DENTAL IMPLANT SURGICAL GUIDE AND MANUFACTURING METHOD THEREOF

(71) Applicant: Mei-Hua Lee, Taipei (TW)

(72) Inventor: Mei-Hua Lee, Taipei (TW)

( * ) Notice: Subject to any disclaimer, the term of this patent is extended or adjusted under 35 U.S.C. 154(b) by 262 days.

(21) Appl. No.: 16/849,667

(22) Filed: Apr. 15, 2020

(65) Prior Publication Data

US 2020/0330185 A1    Oct. 22, 2020

Related U.S. Application Data

(60) Provisional application No. 62/836,415, filed on Apr. 19, 2019.

(51) Int. Cl.

| | | |
|---|---|---|
| *A61C 1/08* | (2006.01) | |
| *A61C 8/00* | (2006.01) | |
| *A61C 5/90* | (2017.01) | |
| *B33Y 10/00* | (2015.01) | |
| *B33Y 80/00* | (2015.01) | |
| *B33Y 50/02* | (2015.01) | |

(Continued)

(52) U.S. Cl.
CPC ............... *A61C 1/084* (2013.01); *A61C 5/90* (2017.02); *B33Y 10/00* (2014.12); *B33Y 50/02* (2014.12); *B33Y 80/00* (2014.12); *A61B 1/00193* (2013.01); *A61B 1/24* (2013.01); *A61C 8/009* (2013.01)

(58) Field of Classification Search
CPC ......... A61C 1/084; A61C 1/082; A61C 8/009; A61C 8/0089; A61B 17/176
See application file for complete search history.

(56) References Cited

U.S. PATENT DOCUMENTS 7,322,821 B1 * 1/2008 Lin ....................... A61C 1/084
433/201.1
2002/0192617 A1 12/2002 Phan et al.
(Continued)

FOREIGN PATENT DOCUMENTS

| CN | 109172011 A | 1/2019 |
|---|---|---|
| TW | I-631937 B | 8/2018 |

(Continued)

OTHER PUBLICATIONS

Office Action dated Sep. 15, 2020 in Taiwan Application No. TW109111560 (15 pages).

*Primary Examiner* — Heidi M Eide
(74) *Attorney, Agent, or Firm* — MUNCY, GEISSLER, OLDS & LOWE, P.C.

(57) ABSTRACT

A dental implant surgical guide and manufacturing method thereof are provided. The dental implant surgical guide comprises a retainer, a guide portion, and an indicator. Said guide portion is located on either the tongue side or the palatal side of a patient, and comprises a guiding groove corresponding to an implant hole and an opening being connected to the guiding groove; said indicator comprises an extension portion and a terminal, wherein the extension portion is extended from the retainer to an implant platform of a missing tooth portion, while the terminal indicates a location of the implant platform. Therefore, locations of the implant platform and the implant hole of the missing tooth portion will be positioned by the dental implant surgical guide when placing the dental implant surgical guide on the missing tooth portion.

7 Claims, 8 Drawing Sheets

(51) Int. Cl.
  *A61B 1/24* (2006.01)
  *A61B 1/00* (2006.01)

(56) References Cited

U.S. PATENT DOCUMENTS

| | | | | |
|---|---|---|---|---|
| 2010/0136500 | A1* | 6/2010 | Suter | A61C 1/084 |
| | | | | 433/75 |
| 2010/0255441 | A1* | 10/2010 | Taormina | B33Y 80/00 |
| | | | | 433/75 |
| 2011/0159455 | A1* | 6/2011 | Stumpel | A61C 1/084 |
| | | | | 700/98 |
| 2014/0322665 | A1* | 10/2014 | Fang | A61C 1/084 |
| | | | | 433/75 |
| 2016/0346062 | A1* | 12/2016 | Lococo | A61C 9/0006 |
| 2019/0374305 | A1* | 12/2019 | Wang | A61C 1/084 |

FOREIGN PATENT DOCUMENTS

| | | | | |
|---|---|---|---|---|
| TW | I-650107 B | | 2/2019 | |
| WO | WO-2006130068 A1 | * | 12/2006 | ............. A61C 1/084 |

\* cited by examiner

DENTAL IMPLANT SURGICAL GUIDE AND MANUFACTURING METHOD THEREOF

CROSS REFERENCE TO RELATED APPLICATION

This application claims the benefit of U.S. Provisional Application Ser. No. 62/836,415 filed on Apr. 19, 2019. The entirety of the Application is incorporated herein by reference.

BACKGROUND OF THE INVENTION

1. Field of the Invention

The present invention relates to a dental implant surgical guide and a manufacturing method thereof. More particularly, the present invention relates to a dental implant surgical guide manufactured according to three-dimensional stereoscopic images and a manufacturing method thereof.

2. Description of Related Art

With the advantages of both aesthetics and long lifetime, dental implant has become one of the main ways to restore missing teeth so far. First, the dentist opens the gums of a missing tooth portion, creates an implant hole by drilling at a predetermined location with a predetermined angle, introduces an implant body into the implant hole, and then sutures the gums. A few months after the implant body is connected to the alveolar bone, a second operation is performed to remove the gums above the implant body and sutures an abutment thereon. After one or two months for the gums to heal, the dentist reconstructs the dental prosthesis on the abutment to complete the whole procedure.

However, in addition to determining the angle, location, and depth for implanting the implant body based on medical records of the patient and image data as X-rays during the operation, it relies heavily on the experiences of the dentist. That is, the dentists may need to peruse higher skills for a perfect implantation. Otherwise, it might be easy to cause instability due to poor angular symmetry if the operation is performed merely based on the location of the bones. An ideal location of the dental implant can not only avoid patients suffering from periodontal disease, but also increase the life span of the dental implant.

Therefore, a dental implant surgical guide with improved positioning accuracy is needed to precisely locate the implant body of the dental implant, thereby reducing the operation time and improving success rate of dental implant operation.

SUMMARY OF THE INVENTION

To solve the problems mentioned above, the object of the present invention is to provide a dental implant surgical guide with improved positioning accuracy. By manufacturing the dental implant surgical guide according to stereoscopic images of an intraoral profile of a patient, locations of healthy teeth, an implant platform, and an implant hole can be positioned more accurately.

Also, by indicating the location of the implant platform under gums through an indicator of the dental implant surgical guide of the present invention, a drilling depth of the implant hole will be indicated, and an implant body can thus be accurately introduced into the implant hole. Hence, the success rate of dental implantation will be improved, and the operation time will be effectively reduced as well.

The dental implant surgical guide of the present invention is used for covering on a missing tooth portion and at least one supporting tooth of a patient to guide locations of an implant platform and an implant hole of the missing tooth portion during a dental implant operation. The dental implant surgical guide comprises a retainer, a guide portion, and an indicator, wherein the retainer is capable of being removably placed on the supporting tooth; the guide portion is located on either a tongue side or a palate side of the patient and is connected to the retainer, wherein the guide portion comprises a guiding groove and an opening, the guiding groove is corresponded to the implant hole and the opening is connected to the guiding groove; the indicator has an extension portion and a terminal, wherein the extension portion is extended from the retainer toward the implant platform of the missing tooth portion, while the terminal indicates the location of the implant platform.

In one embodiment, the retainer comprises an abutment surface accorded with an external contour of the supporting tooth so that the abutment surface is capable of being matched with [the external contour] of the supporting tooth.

In one embodiment, the retainer comprises a widening plate extended from the retainer toward the tongue side of the patient and being placed to abut against a side of the tongue. The size of the widening plate can be adjusted according to the oral cavity of the patient without any limitation.

In one embodiment, the guiding groove is aligned with a buccal side, a lingual side, a mesial side, or a distal side of the implant hole, and guides a direction of the implant hole.

In one embodiment, the guiding groove further comprises a curved surface with a curvature radius in a range of 1 mm to 4 mm. In detail, considering the convenience of introducing the implant body of the dental implant, an entrance of the guiding groove is preferably arc-shaped with an open-end as viewed from the direction of the occlusal plane of the teeth and has a curvature radius. The curvature radius can be designed based on the size of drills and other instruments used in the following procedures or the drilling size of expecting, and is preferably in a range of 1 mm to 4 mm, for example, 1.7 mm, 2.3 mm, or 3.6 mm.

In one embodiment, the guiding groove has a height that is greater than or equal to 6 mm. In this way, instruments as drill pins will be effectively positioned by the guiding groove and thereby operating firmly during the dental implant operation.

In one embodiment, the indicator can further comprise a metal wire disposed on the terminal. The type and the length of the metal wire, for example, can be round or square orthodontic lines commonly used in dentistry with a length in a range of 1 mm to 2 mm. However, the invention is not limited thereto, instead, any metal wire that can be displayed for positioning in X-ray inspection is applicable.

In one embodiment, the dental implant surgical guide may further comprise a plurality of metal positioning members disposed on the retainer. In this way, even on the occasion when a patient has multiple missing teeth or completely edentulous mandible, positioning of teeth can also be accomplished simply by these metal positioning members. The term "plurality" used herein means two or more, such as two, three, four, or five, which can be adjusted according to actual needs. Moreover, embodiments of the metal positioning members, for example, can be metal balls or metal wires or the like without any limitation.

The present invention also discloses a method of manufacturing a dental implant surgical guide, which is used for covering on a missing tooth portion and at least one supporting tooth of a patient to guide locations of an implant platform and an implant hole of the missing tooth portion during a dental implant operation. The method comprises the steps of:
(1) obtaining stereoscopic images showing an intraoral profile of the patient;
(2) obtaining an external contour of the supporting tooth and positioning locations of the implant hole and the implant platform according to the stereoscopic images; and
(3) printing the dental implant surgical guide based on the stereoscopic images by using a three-dimensional printing method, wherein the dental implant surgical guide comprises:
a retainer capable of being removably placed on the supporting tooth;
a guide portion located on either a tongue side or a palate side of the patient and is connected to the retainer, wherein the guide portion comprises a guiding groove and an opening, the guiding groove is corresponded to the implant hole and the opening is connected to the guiding groove; and
an indicator having an extension portion and a terminal, wherein the extension portion is extended from the retainer toward the implant platform of the missing tooth portion, while the terminal indicates the location of the implant platform.

In one embodiment, in step (1), the stereoscopic images are obtained by a digital intraoral scanner, which comprises at least a stereoscopic image of the missing tooth portion, a stereoscopic image of the supporting tooth adjacent to the missing tooth portion, and a stereoscopic image of a location of an alveolar bone of the supporting tooth adjacent to the missing tooth portion. However, methods for obtaining the stereoscopic images are not limited to the digital intraoral scanner, instead, other methods showing three-dimensional images are applicable as well.

In one embodiment, in step (2), the location of the implant hole is positioned by the stereoscopic image of the missing tooth portion; an external contour of the supporting tooth is obtained by the stereoscopic image of the supporting tooth; the location of the implant platform is positioned by the stereoscopic image of the location of the alveolar bone of the supporting tooth.

In one embodiment, in step (3), the retainer comprises an abutment surface accorded with an external contour of the supporting tooth so that the abutment surface is capable of being matched with [the external contour of] the supporting tooth.

In one embodiment, in step (3), the retainer comprises a widening plate extended from the retainer toward the tongue side of the patient and being placed to abut against a side of tongue.

In one embodiment, in step (3), the guiding groove is aligned with a buccal side, a lingual side, a mesial side, or a distal side of the implant hole, and guides the direction of the implant hole.

In one embodiment, in step (3), the guiding groove further comprises a curved surface with a curvature radius in a range of 1 mm to 4 mm. Considering the convenience of introducing the implant body of the dental implant, the curvature radius can be designed based on the size of drills and other instruments used in the following procedures or the drilling size of expecting, for example, 1.7 mm, 2.3 mm, or 3.6 mm.

In one embodiment, in step (3), a height of the guiding groove is greater than or equal to 6 mm. In this way, drilling instruments, such as drill pins, will be effectively positioned by the guiding groove and thereby operating firmly during the dental implant operation.

In one embodiment, in step (3), the indicator further comprises a metal wire disposed on the terminal, and a length of the metal wire is in a range of 1 mm to 2 mm. However, the type and the length of the metal wire are not particularly limited thereto, instead, any metal wire that can be displayed for positioning in X-ray inspection is applicable.

In one embodiment, the method further comprises a step (4) of disposing a plurality of metal positioning members on the retainer. For example, the number of the metal positioning members can be three or more. In this way, even on the occasion when a patient has multiple missing teeth or completely edentulous mandible, positioning of teeth can also be accomplished simply by these metal positioning members.

The present invention further discloses a dental implant surgical guide for dental implant surgery on the occasion when patients who lack health teeth as reference. The dental implant surgical guide is used for covering on a missing tooth portion of the patient to guide locations of an implant platform and an implant hole of the missing tooth portion during a dental implant operation, comprising: a retainer capable of being removably placed on a part of gums of the patient; a guide portion located on either a tongue side or a palate side of the patient and is connected to the retainer, wherein the guide portion comprises a guiding groove and an opening, the guiding groove is corresponded to the implant hole and the opening is connected to the guiding groove; an indicator having an extension portion and a terminal, wherein the extension portion is extended from the retainer toward the implant platform of the missing tooth portion, while the terminal indicates the location of the implant platform, and a plurality of metal positioning members disposed on the retainer. The dental implant surgical guide, which is the same as the embodiment described above, has the guiding groove aligned with a buccal side, a lingual side, a mesial side, or a distal side of the implant hole and guides the direction of the implant hole. The guiding groove also comprises a curved surface with a curvature radius in a range of 1 mm to 4 mm and a height greater than or equal to 6 mm. Furthermore, the indicator may further comprise a metal wire disposed on the terminal with a length between 1 mm to 2 mm so that the metal wire can be displayed for positioning in the following X-ray inspection.

The dental implant surgical guide of the present invention is manufactured by three-dimensional printing after the locations of the implant hole and the implant platform have positioned based on the intraoral stereoscopic images of the patient. Compared with the conventional surgical guide manufactured based on two-dimensional plane images, the dental implant surgical guide of the present invention has the advantages of precise positioning with higher positioning accuracy.

Also, through the indicator, the dental implant surgical guide of the present invention is used for positioning the location and angle when drilling, and thus the implant body can quickly and accurately be introduced into the predetermined location, which not only reduces operation times but also avoids the introduced implant body that has been placed too deep or too shallow. Therefore, the height of the dental implant will be almost the same as the healthy teeth, and the aesthetic and function of the implant can be realized.

The dental implant surgical guide of the present invention further comprises a plurality of metal positioning members disposed on the retainer. In this way, on the occasion when the patient, who has multiple missing teeth, completely edentulous mandible, wearing metal braces, or had accepted dental implants before, will be applied to the present invention.

The above and other features and advantages of the present invention will be described in detail by the following embodiments.

DETAILED DESCRIPTION OF THE PREFERRED EMBODIMENT

Hereinafter, the dental implant surgical guide and the method of manufacturing the dental implant surgical guide of the present invention will be described.

In the present invention, the term "supporting tooth" refers to a healthy tooth adjacent to a missing tooth portion. The term "implant platform" refers to a place located within the missing tooth portion below the bone crest, and is a place located in the extended line of where an upper edge of the alveolar bones of one or two supporting teeth adjacent to the missing tooth portion. The term "facial midline" refers to a dividing line of the front teeth.

Figure 1:
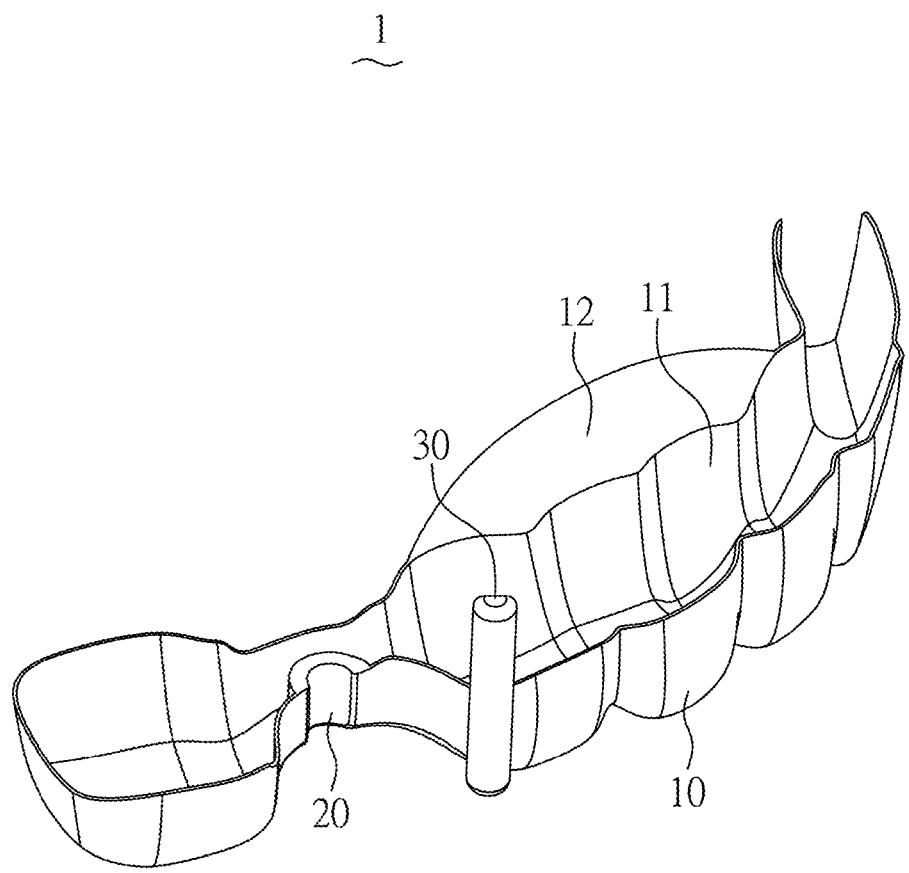
FIG. 1 is a schematic diagram of a dental implant surgical guide according to an embodiment of the present invention.

FIG. 1 is a schematic diagram of a dental implant surgical guide 1 according to an embodiment of the present invention, which comprises a retainer 10, a guide portion 20, and an indicator 30.

Figure 2:
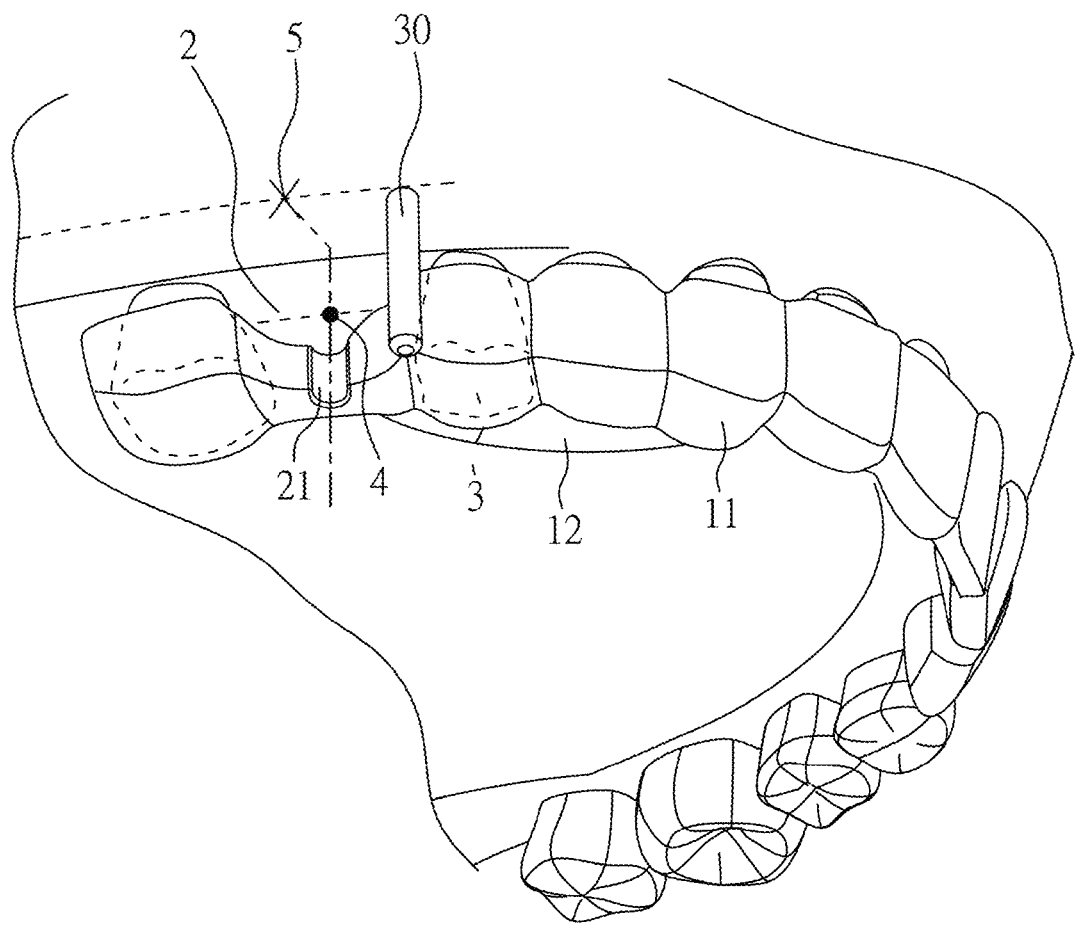
FIG. 2 is a schematic view of the dental implant surgical guide shown in FIG. 1 being placed on the maxillary teeth of a patient.

As shown in FIG. 2, the dental implant surgical guide 1 is being placed on the maxillary teeth of a patient, wherein a specific range, from a missing tooth portion 2, a supporting tooth 3 adjacent to the missing tooth portion 2, to the tooth exceeding the facial midline, is covered by the retainer 10. In another embodiment, the retainer 10 is designed to wider the covering thereof, so that not only the missing tooth portion 2 but every healthy tooth is also covered, but the present invention is not limited thereto.

The retainer 10 comprises an abutment surface 11 that accorded with external contours of these healthy teeth so that the abutment surface 11 is capable of being matched with [the external contour of] the supporting tooth 3. As the abutment surface 11 is being placed to cover these healthy teeth, not only portions or all of the occlusal surface of the healthy teeth but also portions or all of the inside and outside of the healthy teeth near the tongue and/or buccal side are covered by the abutment surface 11.

To maintain the stability of the dental implant surgical guide 1 during the dental implant operation, the retainer 10 comprises a widening plate 12. As shown in FIG. 1, the widening plate 12 is extended from the retainer 10 toward the tongue side of the patient to abut against a side of the tongue to provide additional support.

Figure 3:
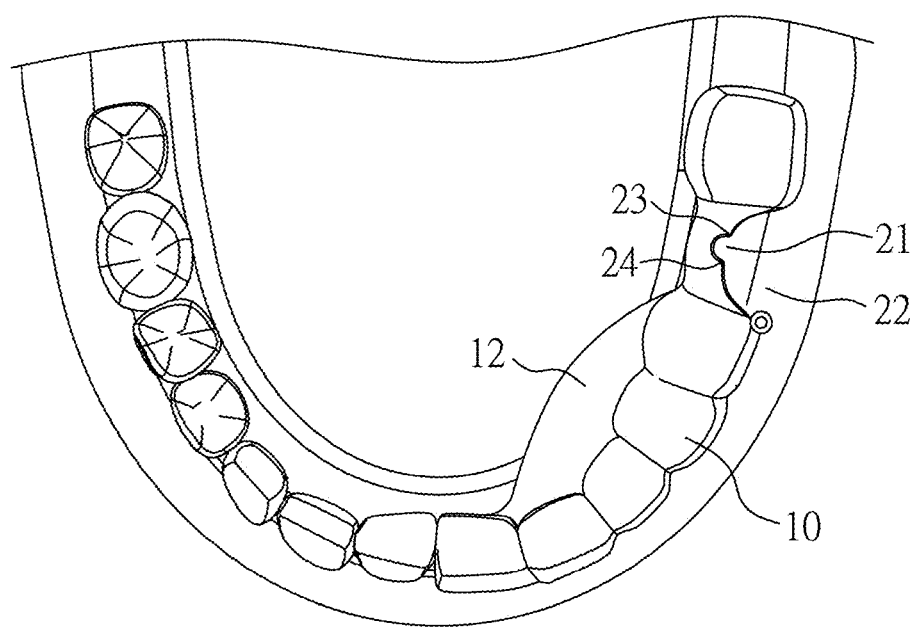
FIG. 3 is a top view of the dental implant surgical guide shown in FIG. 1 being placed on the mandibular teeth of a patient.
Figure 4:
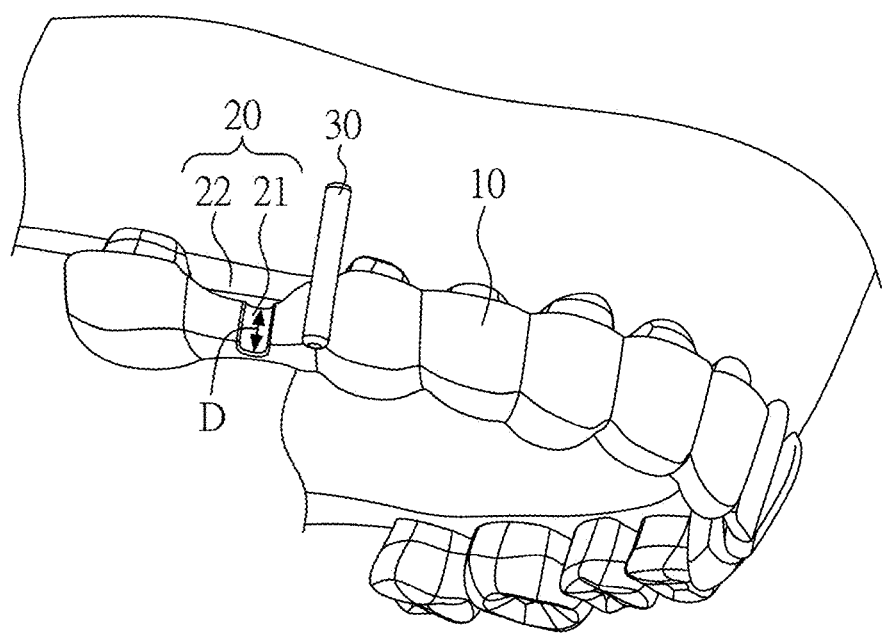
FIG. 4 is a side view of the dental implant surgical guide shown in FIG. 1 being placed on the mandibular teeth of a patient.

As shown in FIG. 2, FIG. 3 and FIG. 4, in which FIG. 3 and FIG. 4 represent a top view and a side view while the dental implant surgical guide 1 is placed on the mandibular teeth of a patient, respectively. The guide portion 20 is connected to the retainer 10 and comprises a guiding groove 21 and an opening 22. Since drilling positioning of an implant hole 4 will need to be accomplished with the guide portion 20 during the dental implant operation, the guiding groove 21 is designed to have an arc-shaped channel with a curved surface to ensure the operation stability of instruments and make instruments easy to entry or exit during the operation. The term "arc-shaped" above refers to a section between two points on a circle. Specifically, as shown in FIG. 3, which is a top view, an entrance of the guiding groove 21 is defined by endpoints 23 and 24 and the arc formed therebetween, and the entrance is formed as a minor arc or a half arc. Moreover, the "guiding groove 21 having an arc-shaped channel with a curved surface" as shown in FIG. 4 is defined by a curved surface that is extended from the endpoints 23, 24 and the arc formed therebetween toward the gums. In the embodiment, a minor arc is defined by endpoints 23, 24 and the arc formed therebetween, in which a virtual circle center subtended by the minor arc has a measure smaller than 180°; a major arc is defined by endpoints 23, 24 and the arc formed therebetween as well, however, a virtual circle center subtended by the major arc has a measure greater than 180°. The minor arc mentioned above belongs to a portion of the guide portion 20 which is connected to the retainer 10, while a portion of the major arc mentioned above is corresponded to the opening 22. Besides, a curvature radius of the guiding groove 21 can be designed based on the size of drills and other instruments used in the following procedures or the drilling size of expecting, for example, 1 mm to 4 mm. Furthermore, as shown in FIG. 4, considering the stability while drilling, a height D of the guiding groove 21 is greater than or equal to 6 mm. The "height D" refers to a distance between the two openings (i.e. the exit and the entrance) of the arc-shaped channel of the guiding groove 21.

The opening 22 can face either the tongue side or the palatal side of the patient, so that the instruments can be entered and exited from a side of the guiding groove 21, having the advantageous for the convenience of moving instruments during the dental implant operation. In FIG. 3 and FIG. 4, the opening 22 is designed to face the palatal side, but in other embodiments, the opening 22 can be designed to face the tongue side without any limitation. Furthermore, since the alveolar bone is covered with gums, it is necessary to open the gums and expose the alveolar bone to confirm the shape of the alveolar bone during the dental implant operation before introduced the implant body. Therefore, a space of the opening 22 can also serve as an accommodation for the opened gums during the alveolar bone confirm procedure.

Figure 5:
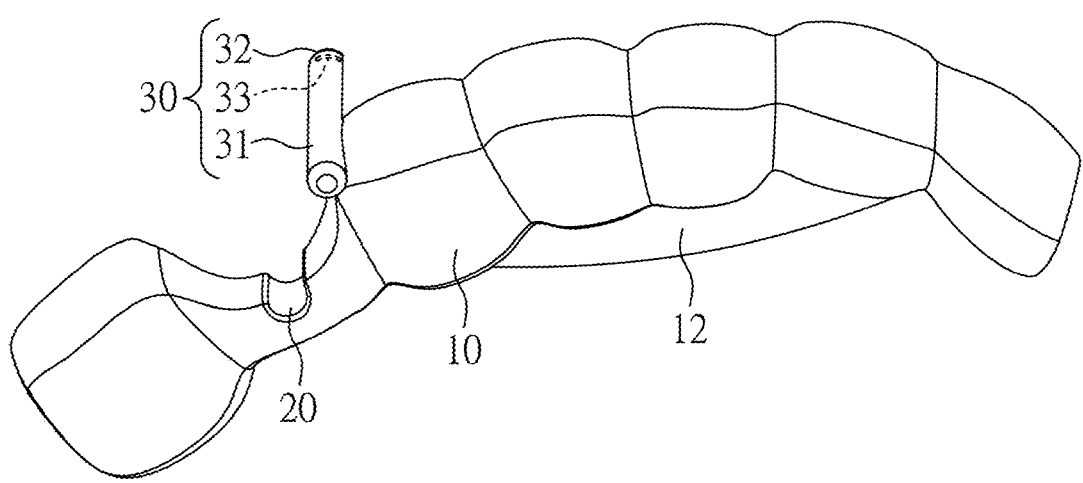
FIG. 5 is a schematic diagram of a dental implant surgical guide according to an embodiment of the present invention.
Figure 6:
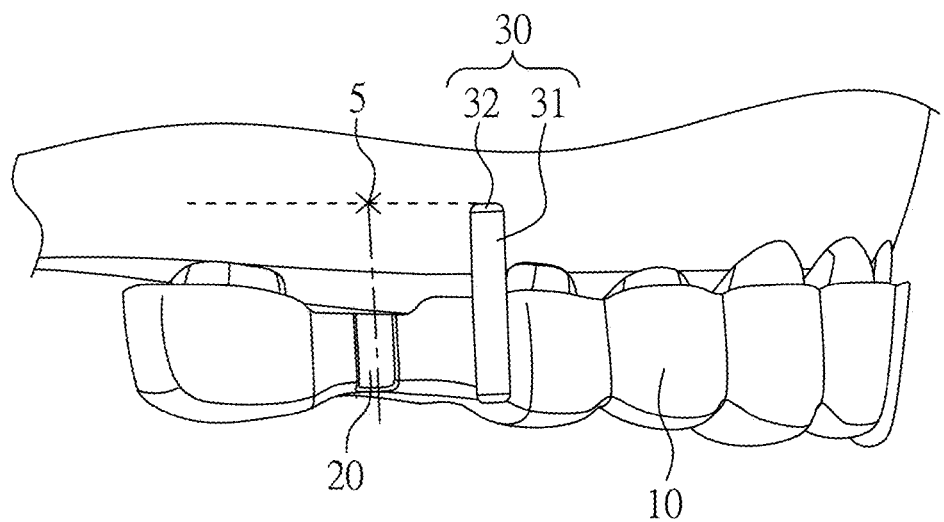
FIG. 6 is a side view of the dental implant surgical guide shown in FIG. 5 being placed on the maxillary teeth of a patient.

In FIG. 2, FIG. 5 and FIG. 6, where FIG. 5 represents a dental implant surgical guide suitable for the maxillary teeth and FIG. 6 is a side view of the dental implant surgical guide shown in FIG. 5 being placed on the maxillary teeth of a patient. The indicator 30 comprises an extension portion 31 and a terminal 32, wherein the extension portion 31 is extended toward the implant platform 5 of the missing tooth portion 2, while the terminal 32 indicates the location of the implant platform 5.

In the embodiment, a metal wire 33 may be disposed on the terminal 32 so that the metal wire 33 can be displayed in the following X-ray inspection for positioning. A length of the metal wire 33 may in a range of 1 mm to 2 mm.

Hence, after the dental implant surgical guide 1 has been placed on teeth and irradiated by X-rays, it can be confirmed whether the location and direction of the guiding groove 21 are correctly aligned with a buccal side, a lingual side, a mesial side, or a distal side of the implant hole. The location of the implant platform 5 may also be confirmed through the metal wire 33 embedded in the terminal 32 by X-rays.

Figure 7:
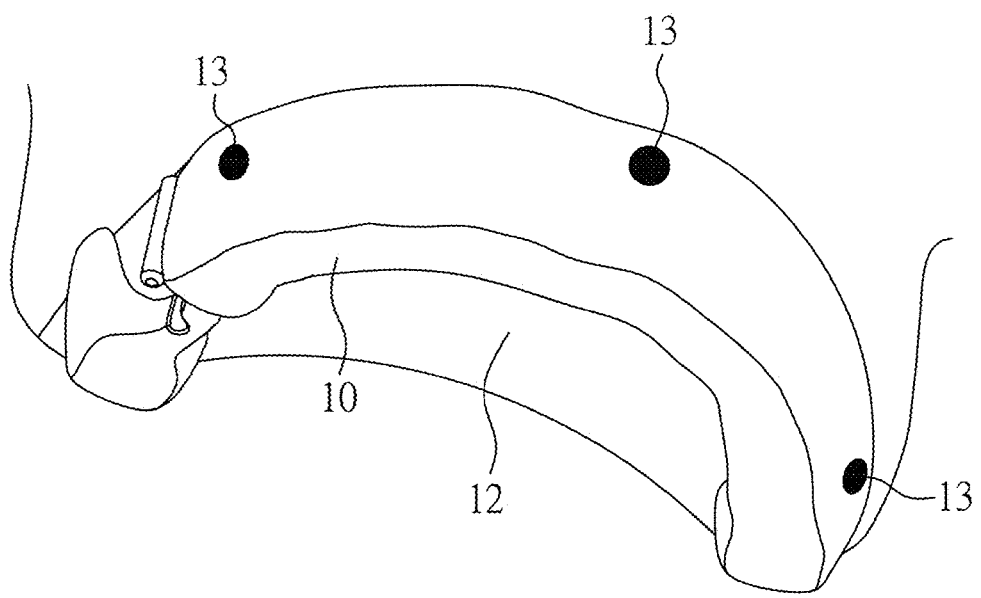
FIG. 7 is a schematic diagram showing metal positioning members disposed on the retainer.

Clinically, even the patient has merely 6 to 8 healthy teeth, the dental implant surgical guide 1 can also be applied for positioning by these healthy teeth. However, for the patient who has multiple missing teeth, completely edentulous mandible, wearing metal braces, or had accepted dental implants before, the positioning is difficult due to the lack of healthy teeth as reference. To solve the problem, another aspect of the dental implant surgical guide is provided, which is mainly disposed a plurality of metal balls as metal positioning members 13 on of the retainer 10, and these metal balls are disposed to be corresponded to the gums, as shown in FIG. 7. In this way, even for patients who are completely edentulous, positioning is possible by the metal positioning members 13 as references through X-rays.

Figure 8:
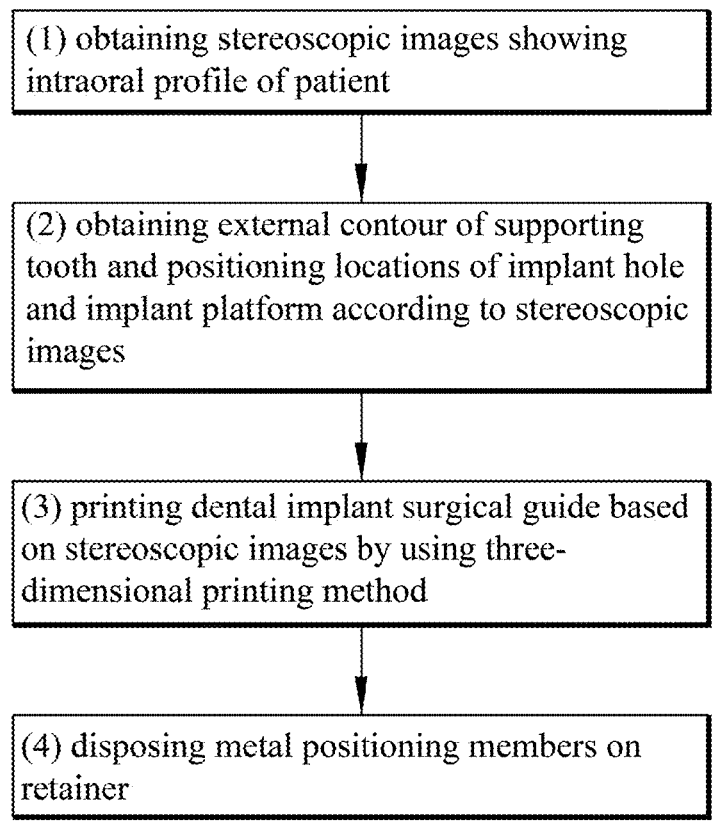
FIG. 8 is a preparation flowchart of manufacturing a dental implant surgical guide according to an embodiment of the present invention.

Next, the manufacturing method of the dental implant surgical guide 1 will be described. Please refer to FIG. 8, which is a preparation flow chart of the dental implant surgical guide of the present invention.

Step (1) is a pre-step to obtain stereoscopic images showing an intraoral profile of the patient. Specifically, a three-dimensional computed tomography scan such as a digital intraoral scanner can be used to perform the intraoral profile of the patient, which can not only present the missing tooth portion 2 and teeth including the supporting tooth 3 adjacent to the missing tooth portion 2, distribution information of bones (such as the location of the alveolar bone of the supporting tooth 3), the paranasal sinuses cavity, and information of important neurovascular tissues may also be collected.

The next step (2) is to perform a positioning procedure according to the stereoscopic images of the intraoral profile of the patient obtained in step (1). Specifically, the location of the implant hole 4 can be positioned by a stereoscopic image of the missing tooth portion 2; an external contour of the supporting tooth 3 can be obtained by a stereoscopic image of the supporting tooth 3, and the location of the implant platform 5 can be positioned by a stereoscopic image of the location of the alveolar bone of the supporting tooth 3.

Step (3) can thus be performed according to the information obtained in the previous steps. The dental implant surgical guide 1 can be printed based on the information obtained in step (2) by using a three-dimensional printing method. The guide portion 20 and the indicator 30 are formed on the dental implant surgical guide 1 to guide locations of the implant hole 4 and the implant platform 5.

If necessary, step (4) may further be included to dispose a plurality of metal positioning members 13 on the retainer 10. In this way, even for a patient who has multiple missing teeth, the dental implant surgical guide 1 of the present invention can still be applied for dental implant operation.

The embodiments above are described by implanting one dental implant as examples, and thus the dental implant surgical guide only comprises one guide portion and one indicator. It should be understood by those skilled in the art that when there are multiple dental implants needed to be implanted, numbers of the guide portion and the indicator will be correspondingly increased depending on conditions of the patient and numbers of dental implants that are going to be implanted in one operation. The changes of increasing and decreasing are also included in the scope of the present invention.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A dental implant surgical guide used for guiding a location of an implant hole including an implant platform to a planned location comprising:
   a retainer comprising an abutment surface capable of being removably placed on supporting teeth on either side of the planned location of the implant hole;
   a guide portion connected to the retainer, wherein the guide portion comprises a guiding groove and an opening, the guiding groove is aligned with a buccal side or a lingual side of the patient with respect to the planned location of the implant hole, and guides a drill for forming the implant hole in the planned location, and the opening is connected to the guiding groove, wherein the guiding groove comprises a curved surface, which is a minor arc or a half arc; and
   an indicator having an extension portion and a terminal, wherein the extension portion extends from the retainer adjacent the guiding groove, towards the planned location of the implant platform of the implant hole along an external surface of the jaw when the retainer is placed on the supporting teeth, while the terminal indicates the drilling depth of the implant hole which is the location of the implant platform, a metal wire embedded in the terminal, and a length of the metal wire is in a range of 1 mm to 2 mm;
   wherein the dental implant surgical guide is manufactured by a three-dimensional printing method.

2. The dental implant surgical guide as claimed in claim 1, wherein the abutment surface comprises an external contour of the supporting tooth so that the abutment surface is capable of being matched with the external contour of the supporting tooth.

3. The dental implant surgical guide as claimed in claim 2, wherein the retainer comprises a widening plate extending from the retainer toward the tongue side of the patient when the retainer is placed on the supporting teeth and being placed to abut against a side of the tongue.

4. The dental implant surgical guide as claimed in claim 1, wherein the curved surface has a curvature radius in a range of 1 mm to 4 mm.

5. The dental implant surgical guide as claimed in claim 1, wherein a height of the guiding groove is 6 mm.

6. The dental implant surgical guide as claimed in claim 1, further comprising a plurality of metal positioning members disposed on the retainer.

7. A dental implant surgical guide used for guiding a location of an implant hole including an implant platform to a planned location, the guide configured to cover a missing tooth portion of a patient who has multiple missing teeth or a completely edentulous mandible, the guide comprising:
- a retainer comprising an abutment surface capable of being removably placed on a part of gums of the patient;
- a guide portion connected to the retainer, wherein the guide portion comprises a guiding groove and an opening, the guiding groove is aligned with a buccal side or a lingual side of the patient with respect to the planned location of the implant hole, and guides a drill for forming the implant hole in the planned location, and the opening is connected to the guiding groove, wherein the guiding groove comprises a curved surface which is a minor arc or a half arc;
- an indicator having an extension portion and a terminal, wherein the extension portion extends from the retainer adjacent the guiding groove towards the planned location of the implant platform of the implant hole along an external surface of the jaw when the retainer is placed on the gums of the patient, while the terminal indicates the drilling depth of the implant hole which is the location of the implant platform, a metal wire embedded in the terminal, and a length of the metal wire is in a range of 1 mm to 2 mm; and
- a plurality of metal positioning members disposed on the retainer;
- wherein the dental implant surgical guide is manufactured by a three-dimensional printing method.

* * * * *